United States Patent [19]

Huber

[11] 4,172,127

[45] Oct. 23, 1979

[54] TREATMENT OF RUMINANTS

[75] Inventor: Thomas L. Huber, Watkinsville, Ga.

[73] Assignee: Research Corporation, New York, N.Y.

[21] Appl. No.: 917,955

[22] Filed: Jun. 22, 1978

Related U.S. Application Data

[62] Division of Ser. No. 610,337, Sep. 4, 1975, Pat. No. 4,112,069.

[51] Int. Cl.$^2$ ............... A61K 35/66; A61K 35/74; A23K 1/16; C12B 1/00

[52] U.S. Cl. ............................................ 424/93; 426/2; 426/61; 426/71; 435/822; 435/260; 435/253; 435/802

[58] Field of Search ............... 424/93; 426/2, 61, 71; 195/30

[56] References Cited

U.S. PATENT DOCUMENTS

| | | | |
|---|---|---|---|
| 2,560,830 | 7/1951 | Turner | 195/28 VB |
| 2,700,611 | 1/1955 | Jeffreys | 426/71 |
| 2,738,273 | 3/1956 | Muhrer | 426/61 |
| 3,243,299 | 3/1966 | Mecho et al. | 426/61 |

FOREIGN PATENT DOCUMENTS

| | | | |
|---|---|---|---|
| 1344321 | 9/1962 | France | 426/61 |
| 1251483 | 10/1971 | United Kingdom . | |

OTHER PUBLICATIONS

Allison et al., J. Anim. Sci., 23 (1964), pp. 1164–1171, (Exhibit B of Ser. No. 610,337).
Drake et al., "Preliminary Investigations with Adapted Rumen Microorganisms" (ARM), Kansas Agr. Ext. Sta. Bul. #536, 5/1/70.
Huber, Am. J. Vet. Res. vol. 35, No. 5, pp. 639–641, May 1974 (Exhibit D of Ser. #610,337).
Kamstra et al., J. Animal Sci. vol. 18, pp. 849–854 (1959).

*Primary Examiner*—Donald B. Moyer
*Attorney, Agent, or Firm*—Cooper, Dunham, Clark, Griffin & Moran

[57] ABSTRACT

In a feedlot operation wherein ruminant animals, such as cattle or sheep, are fed *ad libitum* a high-energy ration or feed, lactic acidosis is greatly reduced or eliminated and weight gain and feed conversion are increased by administering to the animal the microorganism *Peptococcus asaccharolyticus* upon introduction of the animal to the feedlot. The microorganism is conveniently administered to the animal, either by direct injection or introduction into the rumen via a needle or stomach tube or in admixture with the feed or ration. The microorganism is also useful in the treatment of cattle (calves) and sheep ill with lactic acidosis.

15 Claims, No Drawings

TREATMENT OF RUMINANTS

This is a division, of application Ser. No. 610,337 filed Sept. 4, 1975, now U.S. Pat. No. 4,112,069.

This invention relates to the fattening of ruminant animals, such as in a feedlot, wherein the ruminant animal is permitted access ad libitum to a high-energy ration or feed.

One embodiment of this invention is directed to the treatment of ruminant animals before or upon introduction of the animal to a feedlot for fattening.

Another embodiment of this invention is directed to the treatment of ruminant animals, such as cattle or sheep, ill with lactic acidosis.

Still another embodiment of this invention is directed to a high-energy ration or feed which can be usefully employed in a feedlot operation for the fattening of ruminant animals.

Various techniques and feed ration compositions are known and have been employed or suggested in connection with the operation of a feedlot for the fattening of ruminant animals, such as cattle or sheep, see U.S. Pat. Nos. 2,700,611, 2,738,273, 3,857,971, 1,758,937, 3,072,528, 3,243,299, 3,415,225 and 3,875,306. The disclosures of these patents are herein incorporated and made part of this disclosure.

In a feedlot operation wherein a ruminant animal, such as cattle or sheep, is fattened, it has been necessary for the animal to adapt itself to the high-energy ration or feed supplied ad libitum to the animal upon introduction to the feedlot. The period of adaptation usually is about three to four weeks. During this period of adaptation, animal weight gain and feed conversion are far below maximum obtainable and the incidence of lactic acidosis in the animal is substantial.

It is an object of this invention to provide a method whereby a ruminant animal, such as cattle or sheep, upon introduction to the feedlot for fattening by feeding ad libitum on a high-energy ration or diet is substantially immediately adapted to the new high-energy diet or ration with the substantial elimination of lactic acidosis.

It is another object of this invention to provide the treatment of a ruminant animal just prior to introduction of the animal to a feedlot for fattening by means of a high-energy ration or diet whereby animal weight gain and feed conversion are greatly improved.

It is still another object of this invention to provide a method for treating ruminant animals, such as cattle or sheep, ill with lactic acidosis.

How these and other objects of this invention are attainable will become apparent in the light of the accompanying disclosure. In at least one embodiment of the practice of this invention, at least one of the foregoing objects will be achieved.

It has been discovered that a ruminant animal, such as cattle and sheep, can be substantially immediately adapted to a high-energy ration or feed, such as is supplied ad libitum to cattle or sheep in a feedlot operation, by introducing into or establishing in the rumen of the animal a lactic acid-utilizing microorganism. More specifically, it has been discovered that if the microorganism *Peptococcus asaccharolyticus* is introduced into the rumen of a ruminant animal, such as cattle or sheep, prior to or substantially simultaneously with the introduction of the ruminant animal into a feedlot for fattening purposes, the ruminant animal thus treated will be substantially immediately adapted to the high-energy ration or diet employed for fattening, with substantial reduction or elimination of lactic acidosis which usually occurs when a ruminant animal is abruptly supplied with and maintained on a high-energy ration or feed, such as when the animal goes from a substantially hay diet or range foraging to a feedlot for fattening.

Various techniques may be employed for the introduction of the microorganism *Peptococcus asaccharolyticus* into the rumen of the animal. One technique involves the direct injection of the microorganism via a needle into the rumen. Another technique involves the introduction of the microorganism via a stomach tube into the rumen. Another technique useful for the introduction of the microorganism *Peptococcus asaccharolyticus* involves lyophilizing a culture of the microorganism and then reconstituting or regenerating the microorganism and supplying or introducing the resulting regenerated or reconstituted microorganism into the rumen of the animal. Another related technique useful in the practice of this invention involves encapsulating the lyophilized microorganism within a suitable physiologically acceptable carrier, such as a gelatin capsule and the like, and introducing the thus encapsulated, lyophilized microorganism into the rumen of the animal. In this technique, it would be preferred that the rumen or fluid contents of the rumen be brought to a substantially neutral pH, a pH of about 7.0, before the thus encapsulated, lyophilized microorganism is introduced thereinto. Still another technique for the introduction of the microorganism into the rumen for establishing a colony or culture of the microorganism therein involves encapsulating a culture of the microorganism in a suitable physiologically acceptable carrier and introducing the thus encapsulated culture directly into the rumen. In the practices of this invention when a culture of the microorganism *Peptococcus asaccharolyticus* is employed for introduction into the rumen, it is preferred that the culture be in the logarithmic growth phase.

Yet another technique for the introduction of the microorganism into the rumen involves incorporating the microorganism in culture form or in lyophilized form, encapsulated or non-encapsulated, with the feed or ration to be supplied to the animal whereby the microorganism is taken up by the animal along with the feed, thereby entering the rumen where the microorganism will become established.

The microorganism employed in the practices of this invention is, as mentioned hereinabove, the microorganism *Peptococcus asaccharolyticus*. This microorganism is a lactic acid-consumer, and because of this characteristic, when this microorganism is established in the rumen, lactic acidosis in the animal is substantially eliminated.

In accordance with a special embodiment of the practices of this invention, the administration of the microorganism *Peptococcus asaccharolyticus* provides a straightforward, simple and effective method of treatment of animals, such as calves and lambs, suffering from lactic acidosis. When the administration of the microorganism *Peptococcus asaccharolyticus* is employed for therapeutic purposes in the treatment of ruminant animals suffering from lactic acidosis, it is desirable, before the microorganism is administered, to adjust, such as by chemical means, the pH of the rumen or the fluid contents thereof to a substantially neutral pH.

Various amounts of the microorganism, either as a culture thereof, or an encapsulated culture, or a reconstituted or regenerated lyophilized culture, or an encapsulated lyophilized culture, might be employed depending upon the animal, the animal size, the physical condition of the animal, the quality of the microorganism being introduced into the rumen, the method of introduction of the microorganism into the rumen and the like. In the practice of this invention, in order to be effective it is only necessary that the microorganism *Peptococcus asaccharolyticus* be established (and maintained) in the rumen of the animal.

The advantages of the practices of this invention are substantial. Presently, in a feedlot operation, the ruminant animal, e.g. cattle or sheep, is adapted slowly over a period of approximately three weeks. During this period when special high-energy rations are supplied to the animal, the weight gain and feed conversion are far below maximum and the incidences of lactic acidosis may be high. By following the practices of this invention, since the period of adaptation of about three weeks can be substantially eliminated, the feeding period in the feedlot to complete the fattening of the animal is reduced by an equivalent period of time. In view of the cost of feed grains, a three-week reduction in the feeding period of a feedlot operation represents a substantial savings for the feedlot operator and also, as might be apparent, eases the competition between man and animal for cereal grains. As an additional advantage, the shorter feeding period would also reduce the waste disposal problem associated with feedlot operations.

In a feedlot operation, as indicated hereinabove for the fattening of a ruminant animal, such as cattle or sheep, a high-energy ration or feed is employed. In some instances, upon introduction of the animal to the feedlot, a starter feed (less high-energy ration) is employed for about two weeks, followed by a transition feed (somewhat higher-energy ration) for about one week and then, upon adaptation, the animal is supplied with a finishing ration (high-energy feed) for a suitable period of time. Set forth in accompanying Table I are the compositions of rations which might be used in a feedlot operation, including a starter ration (relatively low energy) and a transition ration (relatively higher energy) for adapting the animal to the finishing high-energy ration.

TABLE I

Sample Compositions of Rations Used in Feedlot Operations

| Ingredients | Composition (%) | | |
|---|---|---|---|
| | Starter (14)* | Transition (7)* | Finishing |
| Ground Shelled Corn | 23.4 | 53.4 | 68.4 |
| Soybean Meal | 15.0 | 15.0 | 15.0 |
| Cottonseed Hulls | 60.0 | 30.0 | 15.0 |
| Ground Limestone | 1.0 | 1.0 | 1.0 |
| Trace Mineral Salt | 0.6 | 0.6 | 0.6 |
| Total % | 100.0 | 100.0 | 100.0 |
| Concentrate-Roughage | 40-60 | 70-30 | 85-15 |
| Calculated-Protein | 8.7 | 11.3 | 12.6 |
| TDN | 56.8 | 67.7 | 73.1 |

*=days on ration

In a feedlot operation in accordance with this invention, upon administration of the microorganism *Peptococcus asaccharolyticus* to the rumen of the animal and/or establishment of this microorganism in the rumen thereof and upon introduction of the animal into the feedlot, the animal can be fed directly with the finishing high-energy ration which may have a composition as set forth in accompanying Table II.

TABLE II

Composition of High-Energy Ration

| Ingredients | % by Weight |
|---|---|
| Ground Shelled Corn | 55-80 |
| Soybean Meal | 10-20 |
| Cottonseed Hulls or Peanut Hulls | 7-25 |
| Ground Limestone | about 1.0 |
| Trace Mineral Salt | about 0.6 |
| Concentrate-Roughage | (75-90)-(25-10) |
| Calculated-Protein | 12-15 |
| TDN | about 68-78 |

The following example is illustrative of the advantages obtainable in the practices of this invention:

EXAMPLE NO. 1

Six heifers were administered 1 liter of a medium suitable for the culture of *Peptococcus asaccharolyticus* and six heifers were administered 1 liter of a culture of *Peptococcus asaccharolyticus* in the same medium. The medium and culture were administered via stomach tube and both groups of heifers were immediately fed a high-energy ration containing about 79% ground, shelled corn and 15% by weight soybean meal ad libitum. Feed intake was determined daily and the heifers were weighed two consecutive days prior to inoculation with the medium or culture and at 7 and 14 days and days 21 and 22. The reported on-test and off-test weights are average weights of consecutive weighing days. The results of these tests are set forth in accompanying Table III.

TABLE III

Performance Data of Inoculated Heifers

| Observed Results | Inoculated with Medium | Inoculated with Peptococcus asaccharolyticus Culture |
|---|---|---|
| On-test Weight | 488.8 | 499.3 |
| Off-test Weight | 521.2 | 541.5 |
| Averge Daily Gain | 1.54 | 2.01 |
| Feed/lb. Gain | 8.64 | 6.78 |

Observed weekly average daily gains are set forth in accompanying Table IV.

TABLE IV

| Inoculum | 0-7 | 8-14 | 15-21 |
|---|---|---|---|
| Medium | −.88 | 2.76 | 2.73 |
| Peptococcus asaccharolyticus Culture | −1.61 | 3.24 | 4.40 |

Average daily gain and feed per pound of gain were superior in the heifers inoculated with the *Peptococcus asaccharolyticus* culture. Table IV shows that during the first seven days all heifers lost weight. This early weight loss is usually observed in cattle being adapted to a high-energy ration by conventional procedures. However, the weight gain during the second week for the heifers inoculated with the *Peptococcus asaccharolyticus* culture is higher than for conventional adaptation.

Additional tests demonstrative of the advantages of the practices of this invention are set forth in accompanying Example No. 2.

EXAMPLE NO. 2

In the tests reported in this example, the objectives were: (1) to compare the performance of cattle receiving an inoculum of the microorganism *Peptococcus asaccharolyticus* to cattle receiving no inoculum; (2) to compare the performance of cattle receiving an inoculum of *Peptococcus asaccharolyticus* to cattle receiving an inoculum of rumen fluid from an adapted animal; and (3) to evaluate the effect of an inoculum of *Peptococcus asaccharolyticus* on conventional adaptation during both the adaptation period and the post-adaptation periods.

Procedure:

Thirty-five heifers were maintained on Bermudagrass hay for 25 days prior to the test. The hay was fed once a day in the morning. On-test weights were the average of weights taken two consecutive days prior to the morning feeding. After weighing on the second day, the animals were randomly allotted into 5 groups of seven animals each and started on the test. Test groups were as follows:

Lot 1—Non-inoculated and adapted. The feeding schedule was as follows:

| Feed per Head per Day (lbs.) | | |
|---|---|---|
| | Concentrate | Hay |
| Day 1 | 8 | 5 |
| 2 | 9 | 4 |
| 3 | 10 | 3 |
| 4 | 11 | 2 |
| 5 | 12 | 1 |
| 6 | ad. lib. | " |
| ↓ | | |
| 21 | " | " |

The concentrate was divided into two equal feedings (AM-PM) and the hay was fed once a day (AM).

Lot 2—Inoculated with 1 liter of *Peptococcus asaccharolyticus* culture and immediately full-fed the concentrate ration. These heifers were full-fed throughout the 21-day test period. Full-fed means that the amount fed each day was more than would be consumed.

Lot 3—Non-inoculated and full fed.

Lot 4—Inoculated with 1 liter of strained (cheesecloth) rumen fluid obtained from a rumen cannulated steer full-fed the concentrate ration for three weeks. The animals were full-fed immediately after inoculation and for the remainder of the test period.

Lot 5—Inoculated with 1 liter of *Peptococcus asaccharolyticus* culture and adapted in the exact manner as the animals in Lot 1. After the five-day adaptation period, the animals were full-fed the concentrate ration for the remainder of the test period.

The concentrate ration used in this experiment had a composition as follows:

| Ingredient | Percent of Ration |
|---|---|
| Ground Shelled Corn | 68.4 |
| Soybean Meal | 15.0 |
| Cottonseed Hulls | 15.0 |
| Ground Limestone | 1.0 |
| Trace Mineral Salt | 0.6 |
| Vitamin A 1500 IU/lb. | |

At the time of administration (via stomach tube), the average percent transmittance of the culture was 21 percent (high 27%–low 15%). The cultures were prepared by inoculating 1 liter of media with 7 ml. of a 24-hour culture. The cultures administered to the animals were approximately 13 hours old.

The animals were weighed in the morning on days 7, 14, 21 and 22 of the test period. The off-test weights are averages of weights obtained on days 21 and 22.

Results:

Performance data are presented in Table V.

TABLE V

| | Performance Data for 21-Day Test Period | | | | |
|---|---|---|---|---|---|
| LOT | 1 | 2 | 3 | 4 | 5 |
| Treatment | Adapt | Peptococcus asaccharolyticus Inoculum Full-Fed | Full-Fed | Rumen Fluid Full-Fed | Peptococcus asaccharolyticus Inoculum Adapt |
| On-test wt. (lbs.) | 526 | 526 | 522 | 521 | 522 |
| Off-test wt. (lbs.) | 569 | 584 | 567 | 580 | 571 |
| Average Daily Gains (lbs.) | 2.05 | 2.77 | 2.18 | 2.79 | 2.32 |
| Feed/lb. of Gain (lbs.) | 8.03 | 5.84 | 6.75 | 6.14 | 7.32 |

For the 21-day test period, the animals receiving the *Peptococcus asaccharolyticus* inoculum (LOT 2) had average daily gains and feed efficiency of approximately 22 percent and 14 percent greater than the full-fed non-inoculated cattle (LOT 3).

In the cattle receiving a *Peptococcus asaccharolyticus* inoculum and adapted (LOT 5), the average daily gain and feed efficiency were approximately 11 percent and 9 percent greater than the uninoculated adapted cattle (LOT 1).

Table VI shows the mean daily gains by weight periods.

TABLE VI

| Mean Daily Gains (lbs.) for Each Weigh Period | | | |
|---|---|---|---|
| | Days in Each Period | | |
| Treatment | 0–7 | 8–14 | 15–21 |
| Adapt | −2.88 | 7.18 | 1.86 |
| Peptococcus asaccharolyticus Full-Fed | 0.00 | 5.71 | 2.59 |
| Full-Fed | −0.41 | 4.29 | 2.65 |
| Rumen Fluid Full-Fed | 1.12 | 4.24 | 3.00 |
| Peptococcus asaccharolyticus Adapt | −0.51 | 4.82 | 2.65 |

It would appear that regardless of the feeding method (full-feed or adapt), weight losses occur during the first week or so that the animals are on feed. It is also significant that inoculation either prevented or greatly reduced this early weight loss. By comparing weight gains of period 0-7 days with period 15-21 days, it would appear from this test that the beneficial effect of inoculation observed for the total 21-day test period was realized in the first week or so on feed.

Further experiments were carried out demonstrative of the practices of this invention, particularly for the evaluation of the microorganism *Peptococcus asaccharolyticus* on the performance of steers in a feedlot operation. These experiments are set forth in accompanying Example No. 3.

EXAMPLE NO. 3

Procedure:

Forty-eight head of steers averaging 540 pounds in weight were used in this test. Twenty-four steers were inoculated with a liter of *Peptococcus asaccharolyticus* culture and divided into four lots of six steers each. The 24 control steers were also divided into four lots of six each. Immediately after inoculation, all steers (both treated and controls) were fed the following ration ad libitum.

| Ingredient | Percent |
|---|---|
| Ground Shelled Corn | 75 |
| Supplement (50)% | 5 |
| Peanut Hulls | 20 |
| Trace Mineral | free choice |

Weight gains and feed efficiency were determined weekly for three weeks. The data for the three weeks are summarized in Table VII.

TABLE VII
Performance on Steers Over Three Weeks

| | Inoculated | Control |
|---|---|---|
| No. of Steers | 24 | 24 |
| No. of Replicates | 4 | 4 |
| Beginning Wt. (lbs.) | 543 | 541 |
| Final Wt. (lbs.) | 603 | 593 |
| Average Daily Gain (lbs.) | 2.86 | 2.50 |
| Total Feed (lbs.) | 2231 | 2267 |
| Feed/lb. Gain (lbs.) | 6.18 | 7.19 |
| Average Feed/Day (lbs.) | 17.7 | 18.00 |

Inoculation improved average daily gain by 13 percent and feed efficiency (feed per lb. of gain) by 14 percent. The effect of inoculation upon performance is fairly consistent with the observations of previous experiments.

A summary of all experiments reported herein is as follows:

| | Percent Increase Resulting From Inoculation | |
|---|---|---|
| Experiment | Ave. Daily Gain | Feed Efficiency |
| Example No. 3 | 13 | 14 |
| Inoculation vs. None | 21 | 13 |
| Inoculation vs. Media | 27 | 22 |
| Inoculation Adapt vs. Adapt | 12 | 9 |

Upon continuing the test it was observed that during the two week period of 50-64 days on test the control steers showed an average weight increase of 3.25 pounds per day whereas the inoculated steers showed an average weight increase of 3.50 pounds per day. During the following two week period, 64-78 days on test, and during a period of hot weather when the animals normally do not eat much, the control steers showed an average weight increase of 1.8 pounds per day whereas the inoculated steers averaged an increase of 2.12 pounds per day. These additional data further illustrate the advantages obtainable in the practices of this invention, such as in a feed lot operation for the fattening of cattle.

Although emphasis in the accompanying disclosure in connection with the practices of this invention has been placed on the treatment of cattle or calves and sheep or lambs, as generally indicated, the practice of this invention is applicable to all ruminants. Ruminants which are suitably treated in accordance with this invention, in addition to cattle and sheep, include goat, camel, llama, buffalo, bison, beefalo, deer, antelope and ox or oxen.

It has been disclosed herein that the practice of this invention is applicable to the treatment of ruminants, such as calves or lambs, suffering from lactic acidosis. In accordance with another embodiment of this invention, the practice of this invention is also useful in the treatment of ruminants to prevent rumenitis.

As will be apparent to those skilled in the art in the light of the foregoing disclosure, many modifications, alterations and substitutions are possible in the practice of this invention without departing from the spirit or scope thereof.

I claim:

1. A method which comprises culturing the microorganism *Peptococcus asaccharolyticus*, lyophilizing the resulting culture of said microorganism and administering the resulting lyophilized culture to a ruminant animal to establish a growth of said microorganism in the rumen of said ruminant animal.

2. A method in accordance with claim 1 wherein the lyophilized culture of said microorganism is admixed with water or culture medium before being administered to said ruminant animal.

3. A method in accordance with claim 1 wherein said lyophilized culture is encapsulated in a physiologically acceptable carrier and then administered to said ruminant animal.

4. A method in accordance with claim 1 wherein said lyophilized culture is encapsulated in a physiologically acceptable carrier and then administered to said ruminant animal with the feed.

5. A method which comprises culturing the microorganism *Peptococcus asaccharolyticus* and administering the resulting cultured microorganism to a ruminant animal to establish a growth of said microorganism in the rumen of said ruminant animal.

6. A method in accordance with claim 5 wherein the cultured microorganism is administered directly into the rumen of said ruminant animal.

7. A method in accordance with claim 5 wherein the cultured microorganism is encapsulated in a physiologically acceptable carrier and then administered to said ruminant animal.

8. A method in accordance with claim 5 wherein the cultured microorganism is administered with the feed to said ruminant animal.

9. A high-energy ration or feed suitable for use in a feedlot operation for the fattening of a ruminant animal consisting essentially of a high-energy ration or feed for said ruminant animal and a minor amount of a culture of the microorganism *Peptococcus asaccharolyticus*.

10. A high-energy ration or feed in accordance with claim 9 wherein said high-energy ration or feed contains at least about 50-60% by weight ground, shelled corn or other ceral grains and at least about 5-10% by weight of substantially cellulosic bulking material.

11. A high-energy ration or feed in accordance with claim 9 wherein said high-energy ration or feed contains 60-80% by weight ground, shelled corn or other cereal grains, 5-15% by weight soybean meal or other protein meals and 5-15% by weight seed hulls or other roughages.

12. A high-energy ration or feed in accordance with claim 11 wherein said seed hulls are selected from a group consisting of peanut hulls and cottonseed hulls.

13. A high-energy ration or feed in accordance with claim 9 wherein said high-energy ration or feed contains a culture of said microorganism *Peptococcus asaccharolyticus* in the logarithmic growth phase.

14. A high-energy ration or feed in accordance with claim 9 wherein said high-energy ration or feed contains the culture of the microorganism *Peptococcus asaccharolyticus* encapsulated in a physiologically acceptable carrier.

15. A high-energy ration or feed in accordance with claim 9 wherein said high-energy ration or feed contains the culture of the microorganism *Peptococcus asaccharolyticus* encapsulated as a lyophilized culture in a physiologically acceptable carrier.

* * * * *